(12) United States Patent
Ho et al.

(10) Patent No.: US 7,759,088 B2
(45) Date of Patent: Jul. 20, 2010

(54) STABLE BIODEGRADABLE, HIGH WATER ABSORBABLE γ-POLYGLUTAMIC ACID HYDROGEL BY 3-DIMENSIONAL CROSS-LINKING AND ITS PREPARATION METHOD

(75) Inventors: Guan-Heui Ho, Taipei (TW); Tou-Hsiung Yang, Taichung Hsien (TW); Kung-Hsiang Yang, Taichung Hsien (TW)

(73) Assignee: Tung Hai Biotechnology Corporation, Taichung Hsien (TW)

( * ) Notice: Subject to any disclaimer, the term of this patent is extended or adjusted under 35 U.S.C. 154(b) by 0 days.

(21) Appl. No.: 12/047,752

(22) Filed: Mar. 13, 2008

(65) Prior Publication Data

US 2008/0160569 A1 Jul. 3, 2008

Related U.S. Application Data

(62) Division of application No. 10/740,977, filed on Dec. 19, 2003, now Pat. No. 7,364,879.

(51) Int. Cl.
*C12P 21/06* (2006.01)
*C12P 19/00* (2006.01)

(52) U.S. Cl. .................. 435/68.1; 435/72; 435/74; 435/174; 528/310; 528/328

(58) Field of Classification Search ............... None
See application file for complete search history.

(56) References Cited

U.S. PATENT DOCUMENTS

| | | | |
|---|---|---|---|
| 4,772,419 A | | 9/1988 | Malson et al. |
| 5,610,208 A | * | 3/1997 | Dairoku et al. ........... 525/384 |
| 5,955,549 A | * | 9/1999 | Chang et al. ............. 525/418 |
| 5,986,042 A | | 11/1999 | Irizato et al. |
| 6,072,024 A | | 6/2000 | Irizato et al. |
| 6,288,208 B1 | | 9/2001 | Moshinsky |
| 6,346,569 B1 | | 2/2002 | Irizato et al. |
| 6,495,657 B1 | * | 12/2002 | McDonald et al. .......... 528/310 |
| 6,958,860 B2 | | 10/2005 | Dontula et al. |
| 6,992,144 B2 | | 1/2006 | Dairoku et al. |
| 2004/0019172 A1 | * | 1/2004 | Yang et al. .............. 527/200 |
| 2004/0121905 A1 | | 6/2004 | Ranganathan et al. |

FOREIGN PATENT DOCUMENTS

| | | |
|---|---|---|
| JP | 1-174397 | 7/1989 |
| JP | 5-301904 | 11/1993 |
| JP | 6-322358 | 11/1994 |
| JP | 7-224163 | 8/1995 |
| JP | 7-300563 | 11/1995 |
| JP | 7-309943 | 11/1995 |
| JP | 7-310021 | 11/1995 |
| JP | 1-0298282 | 11/1998 |
| JP | 1-1343339 | 12/1999 |
| JP | 11343339 | * 12/1999 |
| WO | WO 2004/007593 | 1/2004 |

OTHER PUBLICATIONS

English Language Abstract of Japanese Application No. 09-020614 dated Jan. 21, 1997.
English Language Abstract of Japanese Application No. 09-296039 dated Nov. 18, 1997.
English Language Abstract of Japanese Application No. 2002-305975 dated Oct. 24, 2002.
English Language Abstract of Japanese Application No. 2004-210700 dated Jul. 29, 2004.

* cited by examiner

*Primary Examiner*—Herbert J. Lilling
(74) *Attorney, Agent, or Firm*—Scully, Scott, Murphy & Presser, P.C.

(57) ABSTRACT

The present invention relates to a method for the production of a stable biodegradable, high water absorbable γ-polyglutamic acid (γ-PGA) hydrogel by directly cross-linking (A) a γ-polyglutamic acid (γ-PGA), a γ-polyglutamate, or a mixture thereof, and optionally a polysaccharide containing a carboxylic and/or carboxylate group, an amino acid, or a mixture thereof; and/or (B) a microbial culture broth containing a γ-polyglutamic acid (γ-PGA), a γ-polyglutamate, or a mixture thereof, and optionally a polysaccharide containing a carboxylic and/or carboxylate group, an amino acid, or a mixture thereof, with a cross-linker comprising a compound having three or more functional groups or a mixture of a compound having three or more functional groups and a compound having two functional groups, wherein each of the functional groups can react with a carboxylic group (—COOH), carboxylate group (—COO$^-$), aldehyde group (—CHO), hydroxyl (—OH), carbonyl group (—CO), sulfone group (—SO$_2$), amino group (—NH$_2$) or nitro group (—NO$_2$), or a mixture thereof. The present invention further relates to a stable biodegradable, high water absorbable γ-polyglutamic acid (γ-PGA) hydrogel and its uses.

13 Claims, No Drawings

STABLE BIODEGRADABLE, HIGH WATER ABSORBABLE γ-POLYGLUTAMIC ACID HYDROGEL BY 3-DIMENSIONAL CROSS-LINKING AND ITS PREPARATION METHOD

CROSS REFERENCE TO RELATED APPLICATIONS

This application is a divisional application of U.S. patent application Ser. No. 10/740,977, filed on Dec. 19, 2003, now U.S. Pat. No. 7,364,879, issued on Apr. 29, 2008, the contents of which are incorporated by reference.

FIELD OF THE INVENTION

The present invention relates to a stable biodegradable, high water absorbable γ-polyglutamic acid (γ-PGA) hydrogel by 3-dimensional cross-linking, and its preparation method and uses.

BACKGROUND OF THE INVENTION

In recent years, water absorbable hydrogels have been used not only as the materials for paper diapers and tampons, but also as liquid absorbents for use in medical care, construction, civil engineering, building, etc. Moreover, the water absorbable hydrogels can also be used as texture enhancers, fresh-keeping agents for foods, important basal material for greening engineering in the fields of horticulture and other agricultural applications.

Conventional methods for preparing water absorbable hydrogels use starches and celluloses cross-linked with acrylnitrile to form acrylate-based water absorbable hydrogels. Although such acrylate-based hydrogels are cheap, they can be partially decomposed by microorganisms in the soil and encounter difficulties in waste treatment and problems of toxicity toward human bodies. It is believed that imparting water absorbable hydrogels with good biodegradability will resolve the problem regarding the waste treatment. Therefore, there is a great demand for biodegradable, water absorbable hydrogels in view of the increasing environmental concerns.

In order to overcome the aforementioned problem, conventional techniques involve using biodegradable starch-based, hyaluronic acid-based, or polyamino acid-based, or materials as the starting materials for the preparation of biodegradable, water absorbable hydrogels. The methods for the preparation of polyamino acid-based, cross-linked products have been disclosed in the prior art, such as JP 6-322358, JP 7-224163, JP 7-309943, JP 7-300563, JP 10-298282, and JP 11-343339. For example, JP 6-322358 indicates that a solution of γ-PGA can be cross-linked via an electronic polymerization mechanism by using strong gamma-irradiation, so as to form γ-PGA based, cross-linked product. However, the equipments for producing γ-PGA based, cross-linked products through irradiation is very complicated and restricted, such that the production procedure is difficult and inconvenient. JP 11-343339 discloses another method for preparing cross-linked γ-PGA product, comprising isolating a high concentration of γ-PGA from a culture broth, and using the isolated γ-PGA as the starting material for the cross-linking reaction with a di-epoxy compound to obtain a biodegradable, water absorbable hydrogel Nonetheless, such method not only has the drawback associated with the requirement of a high concentration of γ-PGA, obtained through the procedures including a cell separation and extraction of γ-PGA from a microbial culture broth through a refining step, but also requires particular operational equipments to improve the solubility of γ-PGA and the di-epoxy compound in a solvent.

Moreover, the above method uses γ-laser irradiation to complete the cross-linking reaction between γ-PGA and the di-epoxy compound. Obviously, the preparation technology disclosed in JP 11-343339 also causes the problems regarding an increase in cost and inconvenience in preparation procedure.

Moreover, JP 5-301904 discloses polysaccharides produced from *Alcaligenes letus* B116. U.S. Pat. No. 4,772,419 also discloses a method for the preparation of cross-linked polysaccharide products.

Conventional methods for manufacturing cross-linked γ-PGA products require complicated processing procedures, such as the control and operation of complicated irradiation equipments and the separation and refining steps. Also, γ-PGA hydrogel products obtained by known technology are relatively unstable and easily decomposed in few days (3 to 5 days) after fully swelling in water at room temperature. Surprisingly, the inventors of the present application have found that good biodegradable, high water absorbable γ-PGA hydrogels having up to 5,000 times water absorption capacity, improved firmness, and long-term stability after full swelling in water or an aqueous medium can be directly, simply, and successfully prepared.

BRIEF DESCRIPTION OF THE INVENTION

The present invention relates to a method for the production of a stable biodegradable, high water absorbable γ-polyglutamic acid (γ-PGA) hydrogel, by directly cross-linking (A) a γ-polyglutamic acid (γ-PGA), a γ-polyglutamate, or a mixture thereof, and optionally a polysaccharide containing a carboxylic and/or carboxylate group, an amino acid, or a mixture thereof; and/or (B) a microbial culture broth containing a γ-polyglutamic acid (γ-PGA), a γ-polyglutamate, or a mixture thereof, and optionally a polysaccharide containing a carboxylic and/or carboxylate group, an amino acid, or a mixture thereof, with a cross-linker comprising a compound having three or more functional groups or a mixture of a compound having three or more functional groups and a compound having two functional groups, wherein each of the functional groups can react with a carboxylic group (—COOH), carboxylate group (—COO⁻), aldehyde group (—CHO), hydroxyl (—OH), carbonyl group (—CO), sulfone group (—SO₂), amino group (—NH₂) or nitro group (—NO₂), or a mixture thereof.

The present invention further relates to a stable biodegradable, high water absorbable γ-PGA hydrogel prepared by the above method. The inventive γ-PGA hydrogel exhibits good biodegradability, up to 5,000 times water absorption capacity, and improved firmness, and long-term stability after fully swelling in water or an aqueous medium.

DETAILED DESCRIPTION OF THE INVENTION

In the method of the present invention, (A) a γ-polyglutamic acid (γ-PGA), a γ-polyglutamate, or a mixture thereof, and optionally a polysaccharide containing a carboxylic and/or carboxylate group, an amino acid, or a mixture thereof; and/or (B) a microbial culture broth containing a γ-polyglutamic acid (γ-PGA), a γ-polyglutamate, or a mixture thereof, and optionally a polysaccharide containing a carboxylic and/or carboxylate group, an amino acid, or a mixture thereof directly react with a cross-linker comprising a compound having three ore more functional groups or a mixture of a compound having three or more functional groups and a compound having two functional groups. Preferably, γ-PGA with a molecular weight of more than 100,000 Daltons is used. The polysaccharide may be selected from, but is not limited to, a mixture of glucose, fructose, galactose, and glucuronic acid, and a mixture of rhamnose, glucose, galactose, and glucuronic acid, and a polycarboxylic acid in which hyaluronic acid as the principal component. As for the amino acid, it can be selected from, but is not limited to, polyaspartic acid, polylysine, aspartic acid, lysine and arginine, and mixtures thereof.

No special limitation on the other components of the microbial culture broth is necessary. All the components that can be used in a culture broth and that are obvious to persons skilled in the art would be suitable for use in the cultural broth of the present invention. In other words, the culture broth used in the present invention can be prepared by any methods known to persons skilled in the art. For example, JP 1-174397 discloses using a culture broth composed of L-glutanic acid and peptone to grow Bacillus subtilis and Bacillus natto, which can produce γ-PGA.

In the present invention, the species of the compound used as the cross-linker do not require any special limitation. Basically, it is preferred to select a compound having three or more epoxy functional groups or a mixture of a compound having three or more epoxy functional groups and a compound having two epoxy functional groups, such as polyglycidyl ether, as the cross-linker used in the present invention. For example, the polyglycidyl ether can be selected from, but is not limited to, glycerol triglycidyl ether, di- or polyglycerol polyglycidyl ether and polyoxyethylene sorbitol polyglycidyl ether, and a mixture thereof.

In one embodiment of the present invention, the compound having three or more functional groups is glycerol triglycidyl ether and the compound having two functional groups is glycerol diglycidyl ether, and a mixture of them is used as the cross-linker.

The di- or polyglycerol polyglycidyl ether can be a compound of Formula (I):

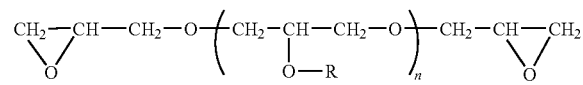

Formual (I)

wherein R is H or

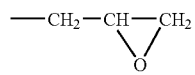

and n is 2 to 8, preferably n is 2 to 4.

The polyoxyethylene sorbitol polyglycidyl ether can be a compound of Formula (II):

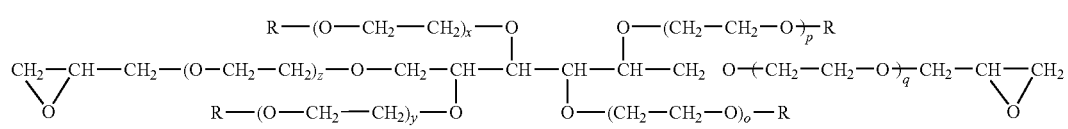

Formula (II)

wherein R is H or

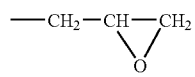

and x, y, z, o, p, and q are independently 1 to 3.

For conducting the cross-linking reaction of the present invention, the amount of the cross-linker, on the basis of the total weight of (A) and (B), is normally 0.02 to 20 wt % and preferably 0.25 to 6 wt %. If the amount of the cross-linker is below 0.02 wt %, the high water absorption rate cannot be achieved because of the insufficient cross-linking. However, if the amount of the cross-linker is greater than 20 wt %, the resulted γ-PGA hydrogels exhibit low water absorbability due to over-cross-linking.

When conducting the aforementioned cross-linking reaction, the cross-linking system is normally maintained at a pH of 3.3 to 8.5, and preferably 4.0 to 8.5. Furthermore, the reaction temperature is between 0° C. and 100° C., and preferably 35° C. and 85° C. Generally, it takes a longer time to complete a reaction conducted at a lower temperature, and on the contrary, a shorter time for the reaction conducted at a higher temperature. Nonetheless, if the reaction temperature is higher than 100° C., undesired side reactions, such as decomposition, will take place and influence the effectiveness of the cross-linking. In addition, carboxylic group (—COOH), carboxylate group (—COO$^-$), aldehyde group (—CHO), hydroxyl (—OH), carbonyl group (—CO), sulfone group ($SO_2$), amino group (—$NH_2$) or nitro group (—$NO_2$), or a combination thereof to the epoxy group provided by the cross-linker is 1:1.

In the method of the present invention, the manner for carrying out the cross-linking reaction does not require any special Limitation. For example, glass reactors equipped with stirrer devices or culture containers shaked in an oil or water bath can be utilized to accomplish the cross-linking reaction involved in the present invention. The method of the present invention may further comprise the steps of hydrating the cross-linked products for swelling, removing the un-cross-linked components by filtration, and drying (e.g., lyophilizing) the prepared water absorbable cross-linked product, to obtain the cross-linked product with high water absorbability.

Apparently, the method of the present invention can produce high water absorbable and stable biodegradable γ-PGA hydrogels more simply and more easily as compared with conventional methods.

The present invention further relates to a stable biodegradable, high water absorbable γ-PGA hydrogel prepared by the above method. The γ-PGA hydrogel of the present invention is effective in terms of water absorption and retention, provides up to 5,000 times water absorption rate, and can be decomposed by microbes existing in the natural environment so that its waste treatment is safer and simpler. Most importantly, since the cross-linker, which comprises a compound having three or more functional groups or a mixture of a compound having three or more functional groups and a compound having two functional groups, is used to conduct the cross-linking reaction, the γ-PGA hydrogel of the present invention has 3-dimensional inter-molecular cross-linked matrix and thus exhibits a longer stability and improved firmness and strength after full swelling in water or an aqueous medium without disintegrating or breaking down even for over 5 weeks in open atmosphere at temperature of 30° C.

The stable biodegradable, high water absorbable γ-PGA hydrogel of the present invention can be used in fields including, among others, the cosmetics fields, as moisturizers or humectants, agricultural and horticultural fields, as soil reconditioning agents, seed-coating agents, water-retaining agents for plant cultivation, immobilizing agents for manure of animals, compost adding agents, or moisturizers for feces, urine, etc.; the civil construction field, as water conditioning agents for water treatment sludge, sewage sludge, and river sewer sludge, solidifying agents, modifying agents, coagulants, or soil for reservoir; medical and hygiene fields, as absorbents for bloods or body fluids, paper diapers or tampons, or as de-odorants or controlled release drug carriers; and the bioengineering fields, as medium base for culturing microbes, plant cells or animal cells, or as immobilizing materials for bioreactors.

Moreover, since γ-PGA hydrogel of the present invention can be prepared by directly reacting the culture broth (Component (B)) with a cross-linker, it will inherently contain the components of the culture broth necessary for the growth of microbes, such as carbon source, nitrogen source, and minerals, and/or metabolites produced by microbes in the culture broth. In view of this property, the biodegradable, water absorbable γ-PGA hydrogel of the present invention is very suitable for use as an agricultural material for compost aids, seed coating agents, and desert greenification materials.

The biodegradable, water absorbable γ-PGA hydrogel of the present invention can be in any desired shapes. For example, the hydrogels can be granulated into a fixed shape or made into irregular shapes, pellets, plates, etc.

The subject invention will be further described by the following examples. Nonetheless, it should be noted that the working examples are provided for an illustration of the present invention, rather than intended to limit the scope of the present invention. EXAMPLE 1

A 300 L culture medium containing 0.5 wt % of yeast extract, 1.5 wt % of peptone, 0.3 wt % of urea, 0.2 wt % of $K_2HPO_4$, 10 wt % of L-glutamic acid, and 8 wt % of glucose and having a pH of 6.8 was added to a 600 L fermentor, and then steam sterilized following the standard procedures. *Bacillus subtilis* was incubated under 37° C. After 96 hours, the culture broth contained 40 g γ-PGA per liter. Each of 15 g of the culture broth was added to 50 ml capped sample bottles into which each of 600 μl of the cross-linkers as listed in Table 1 is introduced. The reaction of the mixtures were conducted at 55° C. for 20 hours in a shaker incubator, rotating at a middle speed.

Each of 1 g of the reacted mixtures were taken out of the 50 ml capped sample bottles and soaked in 800 ml of water at 4° C. overnight. The cross-linked hydrogel formed after hydration and swelling was then filtered through an 80-mesh metal screen and drained to dry. The weights of swollen hydrogels without obvious free water were measured and recorded. The hydrogels were re-soaked in another 800 ml of fresh water at 4° C. in the same beaker overnight. The same procedure was repeated for consecutive 5 days. The cross-linked product was then tested for its water absorption rate as follows:

For the determination of water absorption rate, the cross-linked product was soaked in an excess amount of distilled water and left in the water for swelling overnight to achieve highest hydration. An 80-mesh metal screen was used to filtrate the excess amount of water to obtain the wetted cross-linked product. The wetted cross-linked product was weighed. The water absorption rate is defined as the ratio of the weight of water absorbed (the difference between the wet and dry weights) to the dry weight. The results of the water absorption rate for this example are shown in Table 1.

TABLE 1

| Cross-linker | Reaction time (hr) | Water absorption rate |
|---|---|---|
| Polyethylene glycol diglycidyl ether | 20 | 4,500 |
| A mixture of glycerol triglycidyl ether with glycerol diglycidyl ether | 20 | 4,600 |
| Diglycerol polyglycidyl ether | 20 | 4,880 |
| Polyglycerol polyglycidyl ether | 20 | 4,950 |
| Polyoxyethylene sorbitol polyglycidyl ether | 20 | 4,750 | polyethylene glycol diglycidyl ether is a mixture comprising compounds having the formula of

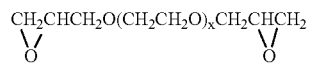

wherein x is 1, 2, 4, 9, 13 or 22

The results listed in Table 1 show that the utilization of either the compound having only two epoxy functional groups, or the compounds having three or more epoxy functional groups or a mixture of a compound having three or more epoxy functional groups and a compound having two epoxy functional groups as the cross-linker can attain at least 4,500 times water absorption rate.

EXAMPLE 2

According to the procedures illustrated in Example 1, samples of 5 wt % sodium γ-PGA solutions and a mixture of glycerol triglycidyl ether with glycerol diglycidyl ether as the cross-linker were used in another set of experiments. The pH was varied as those listed in Table 2. The reacted mixtures were further put into an culture shaker, rotating at a middle speed. The reaction was allowed to continues at 55° C. for 20 hours. After the reaction was completed, the water absorption rates were determined. The results of the water absorption rates of the obtained cross-linked products are listed in Table 2.

TABLE 2

| pH | Water absorption rate |
|---|---|
| 4.0 | 435 |
| 5.0 | 610 |
| 6.0 | 3,450 |
| 8.0 | 4,550 |

EXAMPLE 3

According to the procedures illustrated in Example 1, samples of 5 wt % sodium γ-PGA solutions and diglycerol polyglycidyl ether as the cross-linker were used in another set of experiments. The pH of the solutions was adjusted to 6.5. The amounts of diglycerol polyglycidyl ether listed in Table 3 were used for the cross-linking reaction. The reaction was allowed to continue at 55° C. for 20 hours. The results of water absorption rates of the obtained cross-linked products are listed in Table 3.

TABLE 3

| Amount of cross-linker | Water absorption rate Swelling/hydration time (hr) | | | | |
|---|---|---|---|---|---|
| (%) | 24 | 48 | 72 | 96 | 120 |
| 2 | 450 | 1,250 | 2,550 | 4,350 | 4,450 |
| 3 | 359 | 1,003 | 2,200 | 4,200 | 4,480 |
| 4 | — | — | 2,090 | 4,050 | 4,350 |

EXAMPLE 4

According to the procedures illustrated in Example 1, *Bacillus subtilis* was incubated. The incubation time was altered as shown in Table 4. The pH of the solutions was adjusted to 6.5. A mixture of glycerol triglycidyl ether with glycerol diglycidyl ether was used as the cross-linker. Then, the obtained culture broth was used to conduct cross-linking at 55° C. for 20 hours. The results of the water absorption rates of the obtained cross-linked products are shown in Table 4.

TABLE 4

| Incubation time (hr) | Water absorption rate |
|---|---|
| 24 | a) |
| 36 | a) |
| 48 | 2,600 |
| 60 | 3,050 |
| 72 | 3,000 |
| 84 | 2,880 |
| 96 | 3,550 | a): No cross-linked hydrogel is formed.

EXAMPLE 5

According to the procedures illustrated in Example 1, samples of the culture broth at $96^{th}$ hour (3.8 wt % of γ-PGA) and samples of 3.8 wt % of γ-PGA solutions prepared from purified sodium γ-polyglutamate were used to separately react with diethylene glycol diglycidyl ether and with polyglycerol polyglycidyl ether. The pH of the solutions was adjusted to 6.5. Both of the epoxy compounds were used at 3 wt % of the culture broth or the γ-PGA solution. The cross-linking reactions were allowed to continue at 55° C. for 20 hours. The resulted hydrogel samples were hydrated in excess amount of water at 4° C. for 24 hours. Then, the samples were again hydrated in another fresh water. The same procedure was repeated for 3 consecutive days. The fully swollen hydrogel samples in water were kept at 30° C. in open atmosphere for observing the physical stability and integrity over a period of consecutive 35 days. The soaking water of each hydrogel sample was replaced every 24 hours. The results of the physical stability and integrity of the swollen hydrogel samples were listed in Table 5.

TABLE 5

| Cross-linker (3 wt %) | Stability and integrity Condition observed after samples were placed at 30° C. in open atmosphere | | |
|---|---|---|---|
| | 3 days | 5 days | 35 days |
| Purified γ-PGA with diethylene glycol diglycidyl ether | Partially decomposed | Completely decomposed | — |
| Purified γ-PGA with polyglycerol polyglycidyl ether | Good and firm | Good and firm | Good and firm |
| Culture broth with diethylene glycol diglycidyl ether | Partially decomposed | Completely decomposed | — |
| Culture broth with polyglycerol polyglycidyl ether | Good and firm | Good and firm | Good and firm |

The results in Table 5 show that the utilization of a compound having three or more epoxy functional groups, as the cross-linker can prepare a γ-PGA hydrogel with a high water adsorption rate, long stability after swelling in water, and good biodegradability.

The invention claimed is:

1. A method for the production of a biodegradable, water absorbable γ-polyglutamic acid (γ-PGA) hydrogel comprising directly cross-linking
   (A) a γ-polyglutamate and optionally a polysaccharide containing a carboxylic acid group, and/or carboxylate group, an amino acid, or a mixture thereof; or
   (B) a microbial culture broth containing a γ-polyglutamate and optionally a polysaccharide containing a carboxylic acid group and/or carboxylate group, an amino acid, or a mixture thereof; and
   a cross-linker comprising a polyglycidyl ether having three or more functional groups, wherein the functional groups thereon can react with a carboxylic group (—COOH), carboxylate group (—COO⁻), aldehyde group (—CHO), hydroxyl (—OH), carbonyl group (—CO), sulfone group (—SO₂), amino group (—NH₂) or a nitro group (NO₂) or a mixture thereof, and wherein said polyglycidyl ether is glycerol triglycidyl ether, di- or polyglycerol polyglycidyl ether and polyoxyethylene sorbitol polyglycidyl ether, or a mixture thereof.

2. The method of claim 1, wherein the polysaccharide possesses the constituents selected from the group consisting of a mixture of glucose, fructose, galactose, and glucuronic acid, and a mixture of rhamnose, glucose, galactose, and glucuronic acid.

3. The method of claim 1, wherein the amino acid is selected from the group consisting of polyaspartic acid, polylysine, aspartic acid, lysine and arginine, and a mixture thereof.

4. The method of claim 1, wherein polyglycidyl ether is glycerol triglycidyl ether.

5. The method of claim 1, wherein the di- or polyglycerol polyglycidyl ether is a compound of Formula (I):

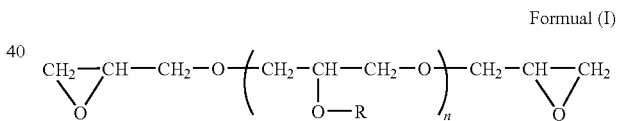

Formual (I)

wherein R is H or

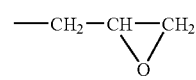

and n is 2 to 8.

6. The method of claim 5, wherein n is 2 to 4.

7. The method of claim 1, wherein the polyoxyethylene sorbitol polyglycidyl ether is a compound of Formula (II):

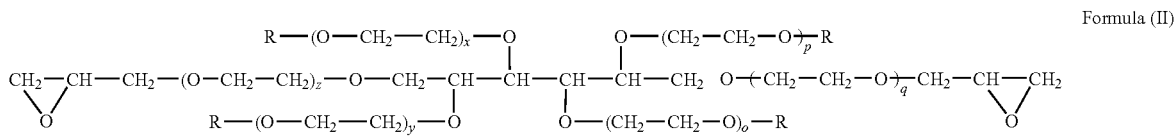

Formula (II)

wherein R is H or

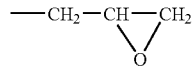

and x, y, z, o, p, and q are independently 1 to 3.

8. The method of claim 1, wherein the amount of the cross-linker is 0.02 to 20 wt %, based on the total weight of (A) and (B).

9. The method of claim 8, wherein the amount of the cross-linker is 0.25 to 6 wt %, based on the total weight of (A) and (B).

10. The method of claim 1, wherein the cross-linking is conducted at a temperature of from 0° C. to 100° C.

11. The method of claim 10, wherein the cross-linking is conducted at a temperature of from 35° C. to 85° C.

12. The method of claim 1, wherein the cross-linking is conducted at a pH of from 3.3 to 8.5.

13. The method of claim 12, wherein the cross-linking is conducted at a pH of from 4.0 to 8.5.

* * * * *